(12) United States Patent
Augello et al.

(10) Patent No.: US 6,821,789 B2
(45) Date of Patent: Nov. 23, 2004

(54) METHOD AND DEVICE FOR COLLECTING AND STABILIZING A BIOLOGICAL SAMPLE

(75) Inventors: Frank A. Augello, Cedar Knolls, NJ (US); Lynne Rainen, Maplewood, NJ (US); Matthew Walenciak, Madison, NJ (US); Uwe Oelmüller, Erkrath (DE); Ralf Wyrich, Grevenbroich (DE); Helge Bastian, Mettmann (DE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/610,554

(22) Filed: Jul. 2, 2003

(65) Prior Publication Data

US 2004/0048384 A1 Mar. 11, 2004

Related U.S. Application Data

(60) Division of application No. 09/984,658, filed on Oct. 30, 2001, now Pat. No. 6,617,170, which is a continuation-in-part of application No. 09/707,745, filed on Nov. 8, 2000, now Pat. No. 6,602,718.

(51) Int. Cl.[7] .......................... G01N 1/00; C12M 1/24; C12M 1/34
(52) U.S. Cl. ..................... 436/176; 436/8; 436/18; 435/2; 435/6; 435/260; 435/287.2; 422/99; 422/102; 252/408.1
(58) Field of Search ................ 436/8, 18, 174, 436/176; 435/2, 4, 6, 269, 270, 287.2; 422/99, 102, 913, 939, 940, 944; 252/408.1

(56) References Cited

U.S. PATENT DOCUMENTS

| | | | |
|---|---|---|---|
| 3,847,738 A | 11/1974 | Brake et al. | 435/2 |
| 4,812,310 A | 3/1989 | Sato et al. | 424/529 |
| 5,300,635 A | 4/1994 | Macfarlane | 536/25.4 |
| 5,459,253 A | 10/1995 | Wolin et al. | 435/6 |
| 5,728,822 A | 3/1998 | Macfarlane | 536/25.41 |
| 5,860,937 A | 1/1999 | Cohen | 210/359 |
| 5,906,744 A | 5/1999 | Carroll et al. | 210/516 |
| 5,932,422 A | 8/1999 | Shyjan et al. | 435/254.2 |
| 6,020,186 A | 2/2000 | Henco et al. | 210/266 |
| 6,258,930 B1 | 7/2001 | Gauch et al. | 241/180 |
| 6,602,718 B1 * | 8/2003 | Augello et al. | 436/176 |
| 6,617,170 B2 * | 9/2003 | Augello et al. | 436/176 |
| 2002/0009722 A1 | 1/2002 | Berger et al. | 435/6 |

FOREIGN PATENT DOCUMENTS

WO        00/09746        2/2000

* cited by examiner

Primary Examiner—Maureen M. Wallenhorst

(57) ABSTRACT

A collection container and method for collecting a predetermined volume of a biological sample, and particularly a whole blood sample, includes at least one gene induction blocking agent in an amount effective to stabilize and inhibit gene induction. The gene induction blocking agent is able to stabilize nucleic acids in the biological sample at the point of collection to block ex vivo gene induction in the sample when stored at room temperature. The stabilizing agents include cationic compounds, detergents, particularly cationic detergents, chaotropic salts, ribonuclease inhibitors, chelating agents, organic solvents, organic reducing reagents, and mixtures thereof. The biological sample is collected directly from the animal and immediately mixed with the gene induction blocking agent without any intermediate processing or handling.

17 Claims, 9 Drawing Sheets

FIG. 2  IFN-gamma mRNA Stability by RT-PCR
Blood Donor 1

FIG. 3  IFN-gamma mRNA Stability by RT-PCR
Blood Donor 2

FIG. 4  IFN-gamma mRNA Stability by RT-PCR
Blood Donor 3

FIG. 5  IFN-gamma mRNA Stability by RT-PCR
Blood Donor 4

METHOD AND DEVICE FOR COLLECTING AND STABILIZING A BIOLOGICAL SAMPLE

CROSS-REFERENCE TO RELATED APPLICATION

This application is a divisional application of Ser. No. 09/984,658 filed Oct. 30, 2001 and now U.S. Pat. No. 6,617,170, issued on Sep. 9, 2003, which is a continuation-in-part application of application Ser. No. 09/707,745, filed Nov. 8, 2000 and now U.S. Pat. No. 6,602,718, issued on Aug. 5, 2003, which are hereby incorporated by reference in their entirety.

FIELD OF THE INVENTION

The present invention is directed to a method and device for collecting, storing, transporting and stabilizing a biological sample, and particularly a whole blood sample, directly from a patient. More particularly, the invention relates to evacuated fluid sample containers having a stabilizing additive contained therein for stabilizing nucleic acids immediately on collection of a biological sample and for inhibiting ex vivo gene induction and degradation during storage.

BACKGROUND OF THE INVENTION

Sample collection containers have been in common use for many years for collecting and storing blood and other body fluids or samples. Typically, the collection containers are glass or plastic tubes having a resilient stopper. These glass or plastic tubes are often used for blood collection.

Blood collection tubes are available where the tube is evacuated to draw a volume of blood into the tube. The tubes can have various additives, such as ethylenediaminetetraacetic acid (EDTA) contained therein for preparing the blood sample for a particular test. A common additive is an anticoagulation agent. Typically, the anticoagulation additive is a buffered citrate or heparin in an aqueous solution. The aqueous citrate is combined with the blood sample in a specified amount to determine the amount of an anticoagulant needed for conducting certain tests. These devices can be used only for serological testing since the additives do not stabilize the nucleic acids in the sample. During shipment, labile RNA molecules are degraded enzymatically so that subsequent RNA separation and analysis is difficult. Furthermore, mechanical irritation or changes of physical conditions such as, for example, temperature or disruption of cells during blood collection and transport causes the induction of gene transcription with the concomitant over- or underproduction of certain mRNA species.

Common additives including anticoagulants to maintain the blood sample in an anticoagulated state are used for performing various processing steps. For example, anticoagulants are typically used in blood samples prior to centrifuging to separate the blood into cell layers. An example of this type of sample tube containing an anticoagulant is disclosed in U.S. Pat. No. 5,667,963 to Smith et al.

In recent years there has been an increase in interest in the field of biological, medical and pharmacological science in the study of gene activities and nucleic acids obtained from biological samples. In particular, ribonucleic acids can provide extensive information of the genetic origin and functional activity of the cell. This information may be used in clinical practice to diagnose infections, detect the presence of cells expressing oncogenes, detect heredity disorders, monitor the state of host defense mechanisms, investigate and diagnostic metabolic diseases, investigate influence of drugs on gene expression in patients, investigate side and toxic effects of drugs, and to determine the HLA type or other marker of identity.

A number of methods exist for isolating RNA which entails disruption of the cell and liberating RNA into solution. Other methods exist for protecting RNA from enzymatic digestion by endogenous RNases. The RNA can then be separated from the DNA and protein, which is solubilized along with the RNA. These processes are usually performed in stepwise fashion rather than for simultaneously lysing cells, solubilizing RNA and inhibiting RNases. Some methods for lysing cells and inhibiting RNases are known that use chaotropic salts of guanidinium.

A commonly used process for isolating RNA involves homogenizing cells in guanidinium isothiocyanate, followed by the sequential addition of sodium acetates and phenol, and chloroform/isoamyl alcohol. After centrifugation, RNA is precipitated from the upper layer by the addition of alcohol. Other methods include the addition of hot phenol to a cell suspension, followed by alcohol precipitation.

Anionic and cationic surfactants are used to lyse cells and liberate cytoplasmic RNA. An example of a method for lysing cells and simultaneously precipitating RNA and DNA from solution is disclosed in U.S. Pat. No. 5,010,183 to Macfarlane. In this process, the RNA is made insoluble. A 2% solution of the surfactant benzyldimethyl n-hexadecylammonium chloride together with 40% urea and other additives are added to a cell suspension. The suspension is then centrifuged to recover a pellet of the insoluble materials. The pellet is resuspended in ethanol and the RNA and DNA are precipitated by the addition of a salt.

A method for analyzing RNA isolated from blood uses amplification methods including polymerase chain reaction to detect sequences of RNA in minute amounts. One difficulty in analyzing RNA is the separation of the RNA from the protein and the DNA in the cell before the RNA is degraded by nucleases. RNase and other nucleases are present in the blood in sufficient quantities to destroy unprotected RNA. Therefore, it is desirable to use a method of isolating RNA from cells in a manner to prevent hydrolysis of RNA by nucleases.

The blood collection methods currently in common use are able to collect and retain the blood for analysis at a later time. The collection device can include an anticoagulant to prevent coagulation during storage. However, the nucleases present in the blood hydrolyze some RNA species during storage and transport while mechanical irritation or changes in physical conditions such as temperature or disruption of cells during blood collection causes induction of some RNA species. These preanalytical sample handling factors result in under- or overrepresentation of mRNA species and eventual degradation of total RNA as determined by molecular diagnostic test methods. In addition, gene induction can result in increased levels of RNA in the sample, which can give false results. Accordingly, there is a continuing need in the industry for an improved method and collection device for blood and other biological samples that preserve the in vivo transcription profile for nucleic acid-based tests.

SUMMARY OF THE INVENTION

The present invention is directed to a method and device for collecting a biological sample. More particularly, the invention is directed to a collection container and to a method of collecting a biological sample and immediately contacting the sample with a stabilizing additive to block ex vivo gene induction in the sample, thereby preserving the in vivo transcription profile.

Accordingly, a primary aspect of the invention is to provide a method and device for collecting a biological sample, and particularly whole blood, directly from a patient in the presence of a stabilizer to stabilize and preserve RNA by inhibiting or blocking gene induction in the sample during storage. The stabilizing additive is present in an effective amount to stabilize the nucleic acids, particularly RNA, and inhibit or block gene induction.

One aspect of the invention is to prepare a biological sample that is stable at room temperature for extended periods of time with little or no occurrence of gene induction. Accordingly, a method is provided for producing a biological sample that is stable at room temperature with little or no incidence of gene induction during storage.

A further aspect of the invention is to provide a method and device for inhibiting gene induction of nucleic acids in a biological sample and to lyse cells, bacteria, viruses and reticulocytes.

Another aspect of the invention is to provide a collection container for receiving and collecting a biological sample where the container is pre-filled with a measured quantity of a gene induction blocking agent.

A further aspect of the invention is to provide a method for stabilizing a biological sample, and particularly whole blood, immediately upon collection from the patient to inhibit or prevent gene induction when the sample is stored at room temperature.

A further aspect of the invention is to provide a method for stabilizing a biological sample, and particularly whole blood, immediately upon collection from the patient to inhibit or prevent gene induction or degradation of nucleic acids when the stabilized blood sample is stored at temperatures below room temperature, typically 2° C. to about 8° C., or at temperatures suitable for archiving the samples, for example, at temperatures of −20° C. to −80° C. Frozen samples can be thawed at room temperature for isolation of nucleic acids.

Still another aspect of the invention is to provide a method for blocking ex vivo gene induction in a biological sample immediately on collection of the biological sample.

Another aspect of the invention is to provide an evacuated container that is pre-filled with an effective amount of a gene induction blocking agent, where the container has an internal pressure sufficiently low to draw a predetermined volume of a biological sample into the container.

A further aspect of the invention is to provide a blood collection container for collecting an amount of blood and mixing the blood with a gene induction blocking agent at the point of collection to produce a biological sample that is stable at room temperature by preventing gene induction such that nucleic acid analysis of the sample can be conducted at a later time.

Another aspect of the invention is to provide a method of stabilizing blood by collecting the blood sample in a container having a gene induction blocking agent and a buffer. The gene induction agent can be a detergent, a chaotropic salt, RNase inhibitors, chelating agents, or mixtures thereof. The pH of the resulting mixture is adjusted to inhibit or block the nucleic acid degradation or gene induction and promote efficient recovery of the analyte.

Still another aspect of the invention is to provide a method of stabilizing a blood sample in a collection device at about pH 2 to about pH 5 in the presence of at least one gene induction blocking agent.

The aspects of the invention are basically attained by providing an apparatus for collecting a biological sample. The apparatus includes a container comprising a side wall, a bottom wall, and an open end defining an internal chamber, and a closure closing the open end. The container includes at least one gene induction blocking agent in an effective amount to preserve the biological sample and block or inhibit ex vivo gene induction. The container can be pre-filled with the stabilizing agent.

The aspects of the invention are further attained by providing a method of preparing a room temperature stable biological sample comprising the steps of: providing a sample collection container having a side wall, and a bottom defining an internal chamber where the container contains at least one gene induction blocking agent in an amount and concentration sufficient to block ex vivo gene induction and preserve a biological sample. A biological sample is obtained and immediately introduced into the container and the biological sample is mixed with the gene induction blocking agent to form a stabilized biological sample.

The aspects of the invention are also attained by providing a method of collecting and stabilizing a whole blood or other biological sample. The method comprises providing a sample collection container having a side wall, a bottom wall and a closure member forming an internal chamber. The container is pre-filled with an effective amount of an aqueous solution or dispersion of a nucleic acid stabilizing agent to stabilize and preserve nucleic acids and/or the transcriptional profile in a whole blood sample. The internal chamber has pressure less than atmospheric pressure. A whole blood sample is collected directly from a patient in the collection container and the blood sample is mixed with the stabilizing agent to form a stable whole blood sample.

These aspects, advantages and other salient features of the invention will become apparent from the annexed drawing and the following detailed description of the invention.

BRIEF DESCRIPTION OF THE DRAWING

The following is a brief description of the drawings, in which.

DETAILED DESCRIPTION OF THE INVENTION

Figure 1:
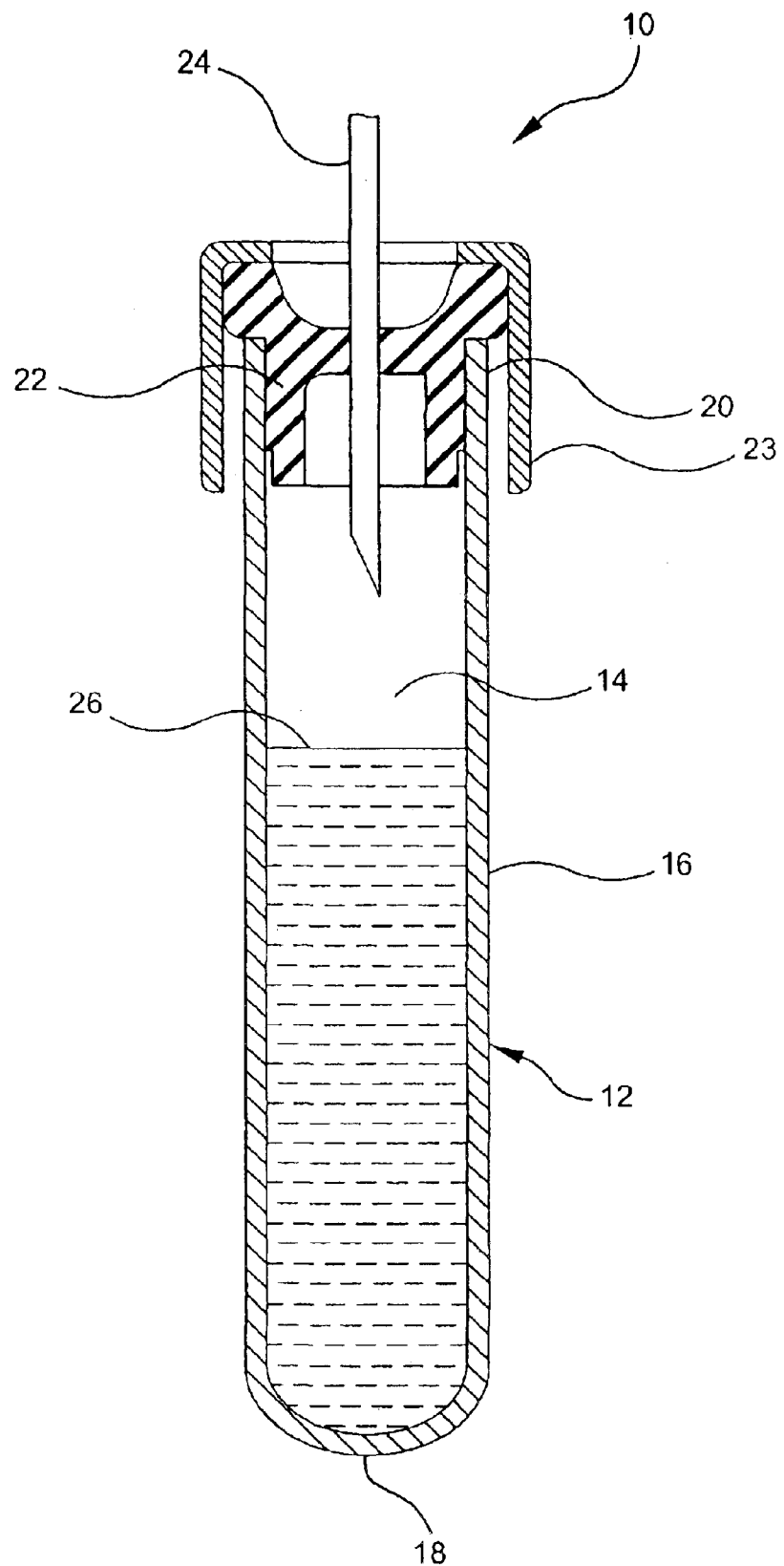
FIG. 1 is a cross-sectional side view of the container in one embodiment of the invention.
Figure 2:
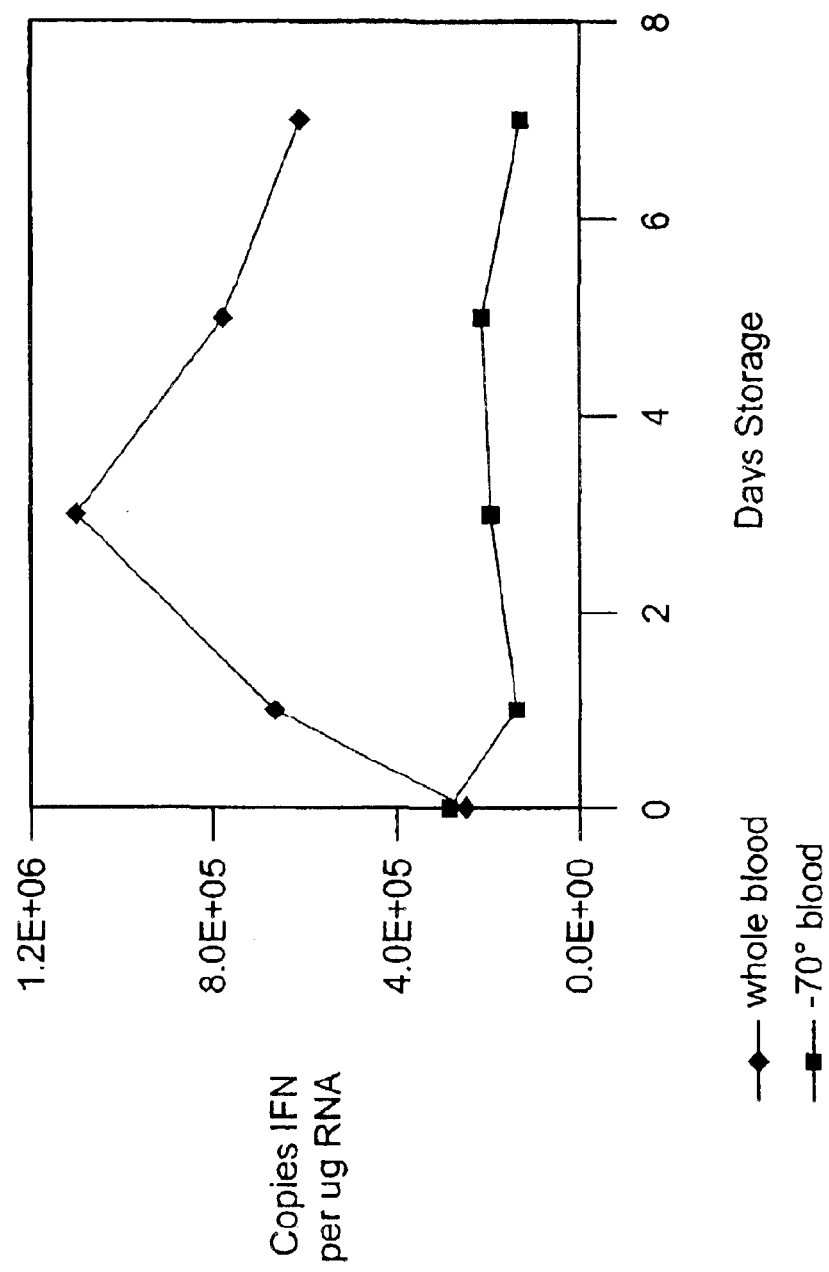
FIG. 2 is a graph showing the changes of the mRNA content of a first blood donor.
Figure 3:
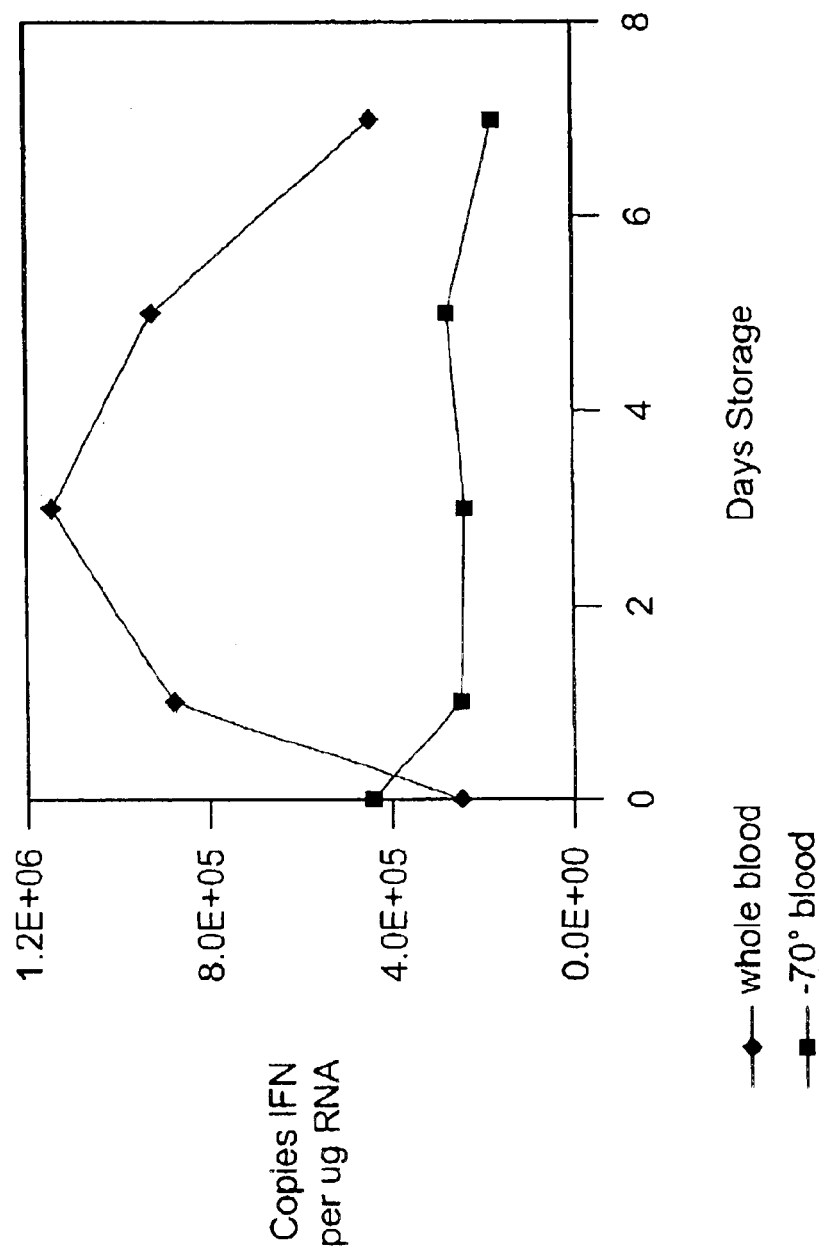
FIG. 3 is a graph showing the changes of the mRNA content of a second blood donor.
Figure 4:
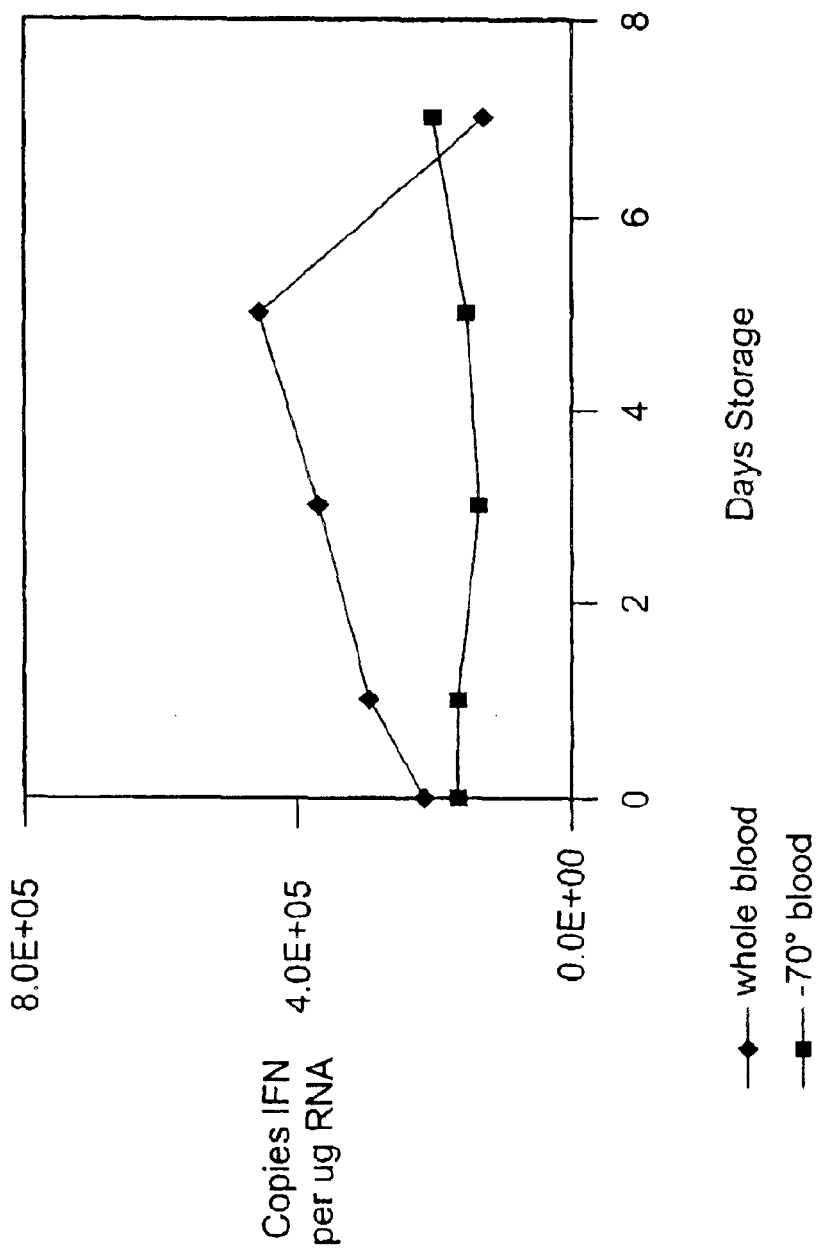
FIG. 4 is a graph showing the changes of the mRNA content of a third blood donor.
Figure 5:
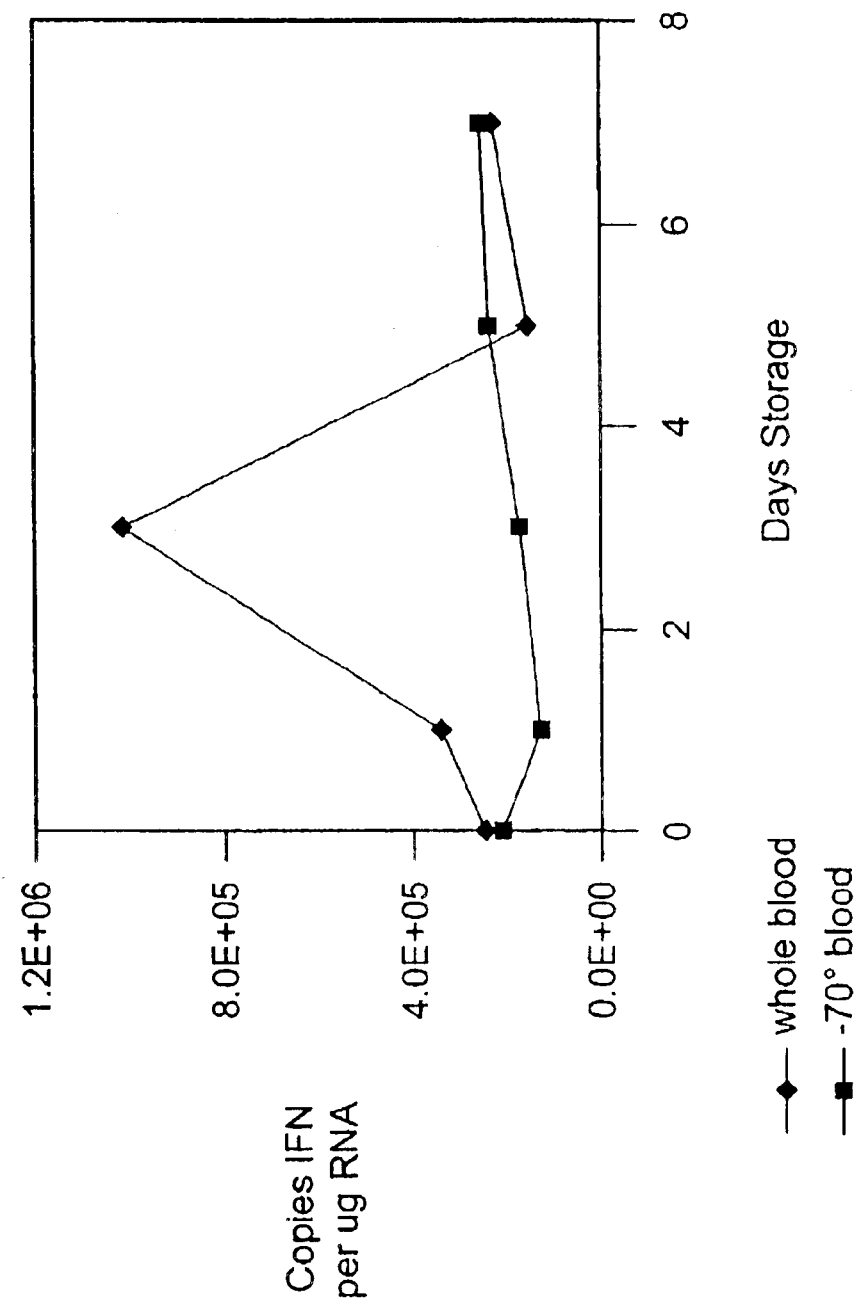
FIG. 5 is a graph showing the changes of the mRNA content of a fourth blood donor.

The present invention is directed to a method and device for stabilizing and preserving a biological sample to enable a determination of in vivo gene transcript numbers with greater accuracy. More particularly, the invention is directed to a method and device for inhibiting or blocking gene induction in a biological sample during collection, transport and storage. In preferred embodiments of the invention, the device is a pre-filled container containing an amount of a gene induction blocking agent for admixing with a biological sample immediately on collection of the sample. The amount of the gene induction blocking agent is preferably included in an amount effective to mix with and stabilize the biological sample. The biological sample is preferably collected directly from an animal, and particularly a human patient.

The biological sample can be a body fluid withdrawn from an animal, and particularly a human patient. In one embodiment, the biological fluid is whole blood. Examples of other biological samples include cell-containing compositions such as red blood cell concentrates, platelet concentrates, leukocyte concentrates, tumor cells, bone marrow, aspirates, tissue, fine needle aspirates and cervical samples. In another embodiment, the biological sample is a body fluid, such as plasma, serum, urine, cerebral spinal fluid, and sputum. The biological sample can also be bacteria and eucaryotic microorganisms. In an embodiment, the biological sample is selected from the group consisting of body fluids, tissues, body swabs and body smears. The gene induction blocking agent of the invention is a suitable agent that is able to inhibit, prevent or reduce the occurrence of ex vivo gene induction during storage of a biological sample. The agent stabilizes the biological sample, such as a blood sample, to produce a room temperature stable composition that inhibits or prevents induced transcription of nucleic acids present in the biological sample.

In one embodiment, the device 10 is a device for drawing a blood sample directly from an animal, and particularly a human patient for stabilizing the nucleic acids and blocking gene transcription immediately at the point of collection. Referring to the figures, device 10 includes a container 12 defining a chamber 14. In the embodiment illustrated, container 12 is a hollow tube having a side wall 16, a closed bottom end 18 and an open top end 20. Container 12 is dimensioned for collecting a suitable volume of a biological fluid. A resilient closure 22 is positioned in open top end 20 to close container 12. Preferably, closure 22 forms a seal capable of effectively closing container 12 and retaining a biological sample in chamber 14. A protective shield 23 overlies closure 22.

Container 12 can be made of glass, plastic or other suitable materials. Plastic materials can be oxygen impermeable materials or contain an oxygen impermeable layer. Alternatively, container 12 can be made of a water and air permeable plastic material. Preferably, chamber 14 maintains a pressure differential between atmospheric pressure and is at a pressure less than atmospheric pressure. The pressure in chamber 14 is selected to draw a predetermined volume of a biological sample into chamber 14. Typically, a biological sample is drawn into chamber 14 by piercing closure 22 with a needle 24 or cannula as known in the art. An example of a suitable container 12 and closure 22 are disclosed in U.S. Pat. No. 5,860,937 to Cohen, which is hereby incorporated by reference in its entirety.

Container 12 is preferably made of a transparent material. Examples of suitable transparent thermoplastic materials include polycarbonates, polyethylene, polypropylene, polyethylene-terephthalate. Container 12 has a suitable dimension selected according to the required volume of the biological sample being collected. In one embodiment, container 12 has a tubular shape with an axial length of about 100-mm and a diameter of about 13-mm to 16-mm.

Closure 22 is made of a resilient material capable of maintaining an internal pressure differential less than atmospheric and that can be pierced by a needle or other cannula to introduce a biological sample into container 12. Suitable materials for closure include, for example, silicone rubber, natural rubber, styrene butadiene rubber, ethylene-propylene copolymers and polychloroprene.

Container 12 also contains a gene induction blocking agent 26 for stabilizing the blood sample. The gene induction blocking agent 26 is preferably a liquid containing a stabilizing agent and is included in an effective amount to mix with the biological sample and stabilize the nucleic acids and block or inhibit gene induction of the cells or nucleic acids contained therein. In one embodiment, the internal pressure of container 12 and the volume of stabilizing additive 26 are selected to provide the necessary concentration of the stabilizing agent for the volume of the biological sample collected. In one preferred embodiment, the internal pressure of container 12 is selected to draw a predetermined volume of about 2.5 ml of a biological sample into container 12 containing an effective volume of gene induction blocking agent 26 for stabilizing the volume of the biological sample. In alternative embodiments, container 12 can have an internal pressure at substantially atmospheric pressure. Preferably, container 12 is pre-filled with the gene induction blocking agent by the manufacturer and packaged in a ready to use form. Typically, the packaged container is sterile and packaged in sterile packaging materials.

In one embodiment, container 12 is made of a plastic that is water and gas permeable. Water loss by evaporation of the stabilizing agent through the permeable wall of the container increases the concentration of the stabilizing agent and decreases the pressure within the container. The diffusion of oxygen through the wall of the tube has the effect of decreasing the vacuum in the container. The water and oxygen permeability properties of the container are selected to maintain the desired pressure differential within the container for the desired shelf life of the container. The shelf life is optimized by balancing the oxygen permeability with the water loss. The container has a shelf life of at least about one year, and preferably longer.

Gene induction blocking agent 26 is a solid or an aqueous solution or dispersion of at least one active stabilizing agent that is included in the container as a pre-filled container. The solid gene induction agent can be a dry powder or particulate such as a spray dried or lyophilized material. The solid gene induction agent can be a loose particulate material contained in the container or a dry coating on the inner surface of the container.

Gene induction blocking agent 26 preferably contains at least one stabilizing agent in a concentration capable of stabilizing nucleic acids in the biological sample, and particularly a whole blood sample. Typically, gene induction blocking agent 26 is an aqueous solution of a stabilizing agent or mixture of stabilizing agents. The stabilizing agents are preferably able to stabilize effectively DNA and RNA including mRNA, tRNA, snRNA, lower molecular weight (LMW)RNA, rRNA and cRNA and are able to block or inhibit ex vivo gene induction in a biological sample during storage at room temperature. Examples of suitable stabilizing agents for stabilizing and preserving nucleic acids and/or preventing gene induction include cationic compounds, detergents, chaotropic salts, ribonuclease inhibitors, chelating agents, quaternary amines, and mixtures thereof. A suitable ribonuclease inhibitor is placental RNAse inhibitor protein. Examples of chaotropic salts include urea, formaldehyde, guanidinium isothiocyanate, guanidinium hydrochloride, formamide, dimethylsulfoxide, ethylene glycol and tetrafluoroacetate. In other embodiments, the gene induction agent is an organic solvent or an organic reducing agent. Examples of suitable organic solvents are selected from the group consisting of phenol, chloroform, acetone and alcohols. The alcohols are generally lower alcohols. Examples of organic reducing agents are selected from the group consisting of mercapto alcohols, di-thio-threitol (DTT), and mixtures thereof.

The stabilizing agent can also include another component for treating the biological sample. For example, chemical agents can be included to permeabilize or lyse cells in the biological sample. Preferably, the stabilizing agent lyses reticulocytes, bacteria, red blood cells and white blood cells. Other components include proteinases, phenol, phenol/chloroform mixtures, alcohols, aldehydes, ketones and organic acids.

The detergents can be anionic detergents, cationic detergents or nonionic detergents. The anionic detergent can be, for example, sodium dodecyl sulfate. Nonionic detergents can be, for example, ethylene oxide condensation products, such as ethoxylated fatty acid esters of polyhydric alcohols. A preferred nonionic detergent is a polyoxyethylene sorbitan monolaurate sold under the trade name TWEEN 20 by Sigma Chemical Co. Another suitable detergent is sodium dodecylsulfate. The detergents are included in an effective amount to lyse the cells. The detergents may also form micelles and other complexes with the nucleic acids and protect RNA and/or DNA by other mechanisms.

In preferred embodiments, the stabilizing agent is a cationic compound having the general formula $YR_1R_2R_3R_4 \, X$, wherein Y is nitrogen or phosphorous; $R_1$, $R_2$, $R_3$, and $R_4$ are independently branched or non-branched alkyl, $C_6$–$C_{20}$ aryl, or $C_6$–$C_{26}$ aralkyl, and X is an organic or inorganic anion. In one embodiment $R_1$, $R_2$, $R_3$, and $R_4$ are independently a $C_3$–$C_{20}$ branched alkyl or a $C_1$–$C_{20}$ non-branched alkyl.

The anion can be an anion of an inorganic acid such as HX where X is fluorine, chlorine, bromine or iodine, with chlorine and bromine being preferred. The anion can also be the anion of a mono-,di- or tricarboxylic acid. Typically, the anion of the cationic compound is selected from the group consisting of phosphate, sulfate, formate, acetate, propionate, oxalate, malonate, succinate, citrate, bromide and chloride.

When $R_1$, $R_2$, $R_3$, and $R_4$ are aryl groups, the aryl groups independently can be, for example, phenyl, lower alkyl-substituted benzyl, and/or halogenated benzyl. In one embodiment $R_1$ is a $C_{12}$, $C_{14}$, or $C_{16}$ alkyl and $R_2$, $R_3$, and $R_4$ are methyl groups. In a preferred embodiment, Y is nitrogen and the stabilizing agent is a quaternary amine. Suitable quaternary amines include alkyltrimethylammonium where the alkyl group has 12, 14 or 16 carbons. One preferred cationic compound is tetradecyltrimethyl ammonium oxalate. Other suitable quaternary amines include alkyltrimethylammonium where the alkyl group includes 12, 14, 16 or 18 carbons. It is generally desirable to have $R_1$, $R_2$, $R_3$, and $R_4$ with 20 carbon atoms or fewer, as alkyl groups having more than 20 carbon atoms can be difficult to solubilize and keep in solution. Examples of suitable quaternary amine surfactants are disclosed in U.S. Pat. No. 5,728,822 to Macfarlane, which is hereby incorporated by reference in its entirety.

In preferred embodiments of the invention the stabilizing agent is a cationic compound and includes a proton donor in an amount effective to stabilize nucleic acids. It has been found that the addition of a proton donor to the cationic compounds increases the ability of the cationic compounds to stabilize the nucleic acids in the biological sample. Examples of suitable proton donors include monocarboxylic acids, dicarboxylic acids, tricarboxylic acids, aliphatic keto-dicarboxylic acids, amino acids, mineral acids and mixtures thereof. In one embodiment, the proton donor is selected from the group consisting of alkenyl carboxylic acids, $C_1$–$C_6$ aliphatic monocarboxylic acids, aliphatic $C_2$–$C_6$ dicarboxylic acids, tricarboxylic acids, hydroxy-monocarboxylic acids, hydroxy-dicarboxylic acids, hydroxy-tricarboxylic acids, aliphatic keto-monocarboxylic acids, aliphatic keto-dicarboxylic acids, amino acids, and mixtures thereof. Examples of suitable aliphatic carboxylic acids include $C_1$–$C_6$ alkyl carboxylic acids, such as acetic acid, propionic acid, n-butanoic acid, n-pentanoic acid, isopentanoic acid, 2-methylbutanoic acid, 2,2 dimethylpropionic acid, n-hexanoic acid, n-octanoic acid, n-decanoic acid, and dodecanoic acid. Examples of alkenyl carboxylic acids include acrylic acid, methacrylic acid, butenoic acid, isobutenoic acid and mixtures thereof.

The dicarboxylic acids of the proton donor in one embodiment are selected from the group consisting of oxalic acid, malonic acid, succinic acid, glutaric acid, adipic acid and mixtures thereof. Examples of hydroxyl-containing acids include tartaric acid and malic acid. Suitable amino acids are selected from the group consisting of glycine, alanine, valine, leucine, iso-leucine and mixtures thereof. The tricarboxylic acids of the proton donor can be selected from the group consisting of citric acid and iso-citric acid.

The quantity of gene induction blocking agent 26 in container 12 is determined by the internal volume of container 12, the internal pressure and the volume of the biological sample drawn into the container. In the illustrated embodiment, container 12 has an axial length of about 100-mm and a diameter of about 16-mm and has an internal pressure to draw a biological sample of about 2.5-ml. Stabilizing additive 26 typically contains about 50 mg to about 90 mg per ml of the carrier liquid. Preferably, gene induction blocking agent 26 is an aqueous medium containing about 60 mg/ml to about 80 mg/ml, and most preferably about 70 mg/ml. The volume of stabilizing additive 26 in container 12 is about 6 to 8 ml, and preferably about 7 ml.

In one preferred embodiment, gene induction blocking agent 26 includes about 70 mg/ml of a nucleic acid stabilizing agent able to block or inhibit ex vivo gene induction and is mixed with whole blood drawn directly from a patient. The blood is mixed with the liquid in a ratio of about 1:2 to about 1:3.5, preferably about 1:2.5 to about 1:3.1, and most preferably about 1:2.7 to about 1:2.8 by volume.

The concentration of the stabilizing agent is sufficient to stabilize the nucleic acids and block or inhibit ex vivo gene induction. In one preferred embodiment, the biological sample is whole blood. The concentration of the stabilizing agent after mixing with blood is about 45 mg/ml to about 55 mg/ml of the mixture, preferably about 50 mg/ml to about 53 mg/ml, and more preferably about 51 mg/ml to about 52 mg/ml.

The method of the invention is performed by obtaining a biological sample and introducing the sample into the container containing the gene induction blocking agent. In preferred embodiments the biological sample is prepared and immediately introduced directly into the collection container. In preferred embodiments, the biological sample is withdrawn from the patient directly into the collection container without any intervening process or handling steps so that the sample mixes with the gene induction blocking agent immediately to prevent or inhibit nucleic acid decomposition. It has been found that collecting the biological sample directly from the patient, such as when collecting a whole blood sample, and introducing the sample directly into the container containing the stabilizing agent substantially prevents or reduces the gene transcription and the decomposition of the nucleic acids that otherwise occur when the sample is stored before combining with the stabilizing agent. It has been found that combining the biological sample with the gene induction blocking agent immediately upon collection or preparation of the biological sample reduces or prevents ex vivo gene induction during storage of the biological sample.

The cationic compounds are preferred stabilizing agents. The cationic compounds produce a stabilized whole blood sample that can be transported at ambient temperature or below room temperature to a laboratory where the nucleic acids can be isolated from the sample. The stabilized whole blood sample can also be stored and transported at a temperature lower than room temperature, for example, at about 2° C. to about 8° C. The stabilized whole blood sample can also be stored under conditions where it is frozen. For longer storage and archiving, the samples can be stored at about −20° C. For later nucleic acid isolation, the sample can be thawed and further processed. It has been found that the stabilizing agents allow reliable freezing of blood samples for later RNA isolation. Biological samples, and particularly blood samples when frozen without the stabilizing agents, exhibit nucleic acid and particularly RNA degradation during the thawing process. In other embodiments, the biological samples can be stored at about 0° C. to about −80° C., and preferably at about 0° C. to about −70° C.

It has been found that the recovery and stabilization of nucleic acids in the biological sample is dependent on the pH of the biological sample and stabilizing agent. The pH of the resulting mixture can range from about pH 2 to about pH 12, preferably about pH 2 to about pH 10, and more preferably about pH 3 to about pH 8. The life of the nucleic acids in this range will vary depending on the biological sample, the ratio of the amount of the biological sample to the amount of the stabilizing agent, and the particular stabilizing agent used. The shelf life of the stabilized nucleic acids in this pH can range from about 24 hours to several days at room temperature. The shelf life of the stabilized nucleic acids in the pH range can be up to several weeks in a refrigerator at about 2° C. to about 8° C. The stabilized nucleic acids can be archived frozen at −20° C. or at lower temperatures, for example, −70° C. to −80° C.

The pH of the resulting mixture will vary depending on the biological sample being stabilized. In one embodiment of the invention, the biological sample is whole blood and the mixture of the whole blood and the stabilizing agent is adjust to about pH 2 to about pH 5. Nucleic acids stabilized with cationic compounds adjusted to about pH 2 to about pH 5 are stable at ambient temperature for several days or at 2° C. to about 8° C. for several weeks or can be archived frozen at temperatures of −20° C. or below. It has been found that optimum long term stabilization of nucleic acids in the mixture of whole blood and the stabilizing agent is obtained at about pH 3.9 to about pH 4.1.

The stabilizing solution in the collection device in one preferred embodiment has an optimal pH of about 3.6 to about 3.8 before a biological sample is added. After a blood sample is added to the collection device and mixed with the stabilizing solution, the resulting mixture has a pH of about 3.9 to about 4.1. In a preferred embodiment, the collection device includes an amount of a stabilizing agent such that when mixed with whole blood in a blood to stabilizing agent ratio of about 1:2.5 to about 1:3.1 by volume, the resulting mixture has a pH of about 3.9 to about 4.1. In other biological samples, the pH is adjusted appropriately to stabilize the mixture. For example, it has been found that eucaryotic cell cultures are stabilized at pH 4 to about pH 8, and preferably at about pH 6 to about pH 8.

The pH of the mixture of the biological sample and stabilizing agent can be adjusted by the addition of a suitable buffer. An example of a buffer that has been found to be effective in adjusting the pH of the biological sample is tartaric acid. Other buffers and pH adjusting agents as known in the art can also be used. The pH of the buffer can be adjusted to the desired range by the addition of sodium hydroxide.

The nucleic acids, either DNA or RNA can be separated from the stabilized biological sample using various processes as known in the art. It has been found that the stabilizing agents can be separated from the nucleic acids during the purification protocol performed in the laboratory to yield the purified nucleic acid.

Cationic compounds cause lysis of the cells and virus in the sample and cause precipitation of the nucleic acids in a complex with the compound. The precipitated nucleic acids can be extracted from the complex by a phenol extraction or by a formamide buffer as known in the art. In a further embodiment, the detergent can, be solubilized to disassociate the complex and leave the insoluble nucleic acids. The compound can be solubilized by treating the complex with a concentrated solution of lithium chloride or other high salt solutions as, for example, guanidinium isothiocyanate or guanidinium hydrochloride. Other methods of isolating and purifying nucleic acids are disclosed in U.S. Pat. No. 5,990,301 to Colpan et al., which is hereby incorporated by reference in its entirety.

EXAMPLE 1

Stabilization of RNA in Human Blood

This example demonstrates the effects of the ratio of the blood to stabilizing agent and the concentration of the stabilizing agent.

Twenty-four samples were prepared for this comparison. Each sample was prepared from 2.5 ml blood, drawn with a sodium citrate containing blood collection device, and mixed with 7.5 ml of a stabilization buffer containing 3% (w/v) tetradecyltrimethylammonium oxalate and 125 mM and 200 mM tartaric acid, respectively, in a 12 ml polyethylene tube. The pH of the buffer was adjusted with sodium hydroxide to 3.3, 3.5 and 3.7, respectively. Samples were stored at room temperature for 25 hours and 72 hours, respectively. In order to isolate the cellular RNA, the tubes were centrifuged at 5000×g for 10 minutes. The supernatant was discarded and the pellet was washed once with water. After additional centrifugation at 5000×g for 10 minutes, the pellet was dissolved in 300 µl of a lysis buffer, i.e., buffer RLT (QIAGEN GmbH), diluted with 360 µl water and 40 µl proteinase K were added. After a proteinase digestion for 10 minutes at 55° C. the sample was centrifuged at 20,000×g for 3 minutes, the supernatant was transferred into a new tube and 350 µl of 98% ethanol were added. The sample was then applied to a silica membrane containing spin column via centrifugation at 8000×g for 1 minute. The spin column was washed once with a GITC containing washing buffer-like buffer RW1 (QIAGEN GmbH) and two times with an ethanol wash containing buffer-like buffer RPE (QIAGEN GmbH). The RNA was then eluted from the silica membrane with 2×40 µl of RNase free water. All samples were processed in duplicates.

The yield of the isolated RNA was determined by measuring the optical density at 260 nm wavelength in a spectrophotometer and calculating that 1 OD260 corresponds to a concentration of 40 µg RNA/ml. The integrity of the isolated RNA was proved by electrophoresis of 30 µl of the eluate in a denaturating agarose/formaldehyde gel, stained with ethidium bromide. The yield of the RNA is presented in Table 1 and Table 2.

TABLE 1

125 mM Tartaric Acid

| Sample | pH | Storage Time (hours) | Yield (µg) |
|---|---|---|---|
| 1 | 3.3 | 24 | 8.4 |
| 2 | 3.3 | 24 | 7.6 |
| 3 | 3.5 | 24 | 9.5 |
| 4 | 3.5 | 24 | 9.8 |
| 5 | 3.7 | 24 | 13.3 |
| 6 | 3.7 | 24 | 17.2 |
| 7 | 3.3 | 72 | 7.2 |
| 8 | 3.3 | 72 | 6.8 |
| 9 | 3.5 | 72 | 10.3 |
| 10 | 3.5 | 72 | 10.9 |
| 11 | 3.7 | 72 | 14.8 |
| 12 | 3.7 | 72 | 16.1 |

TABLE 2

200 mM Tartaric Acid

| Sample | pH | Storage Time (hours) | Yield (µg) |
|---|---|---|---|
| 13 | 3.3 | 24 | 5.9 |
| 14 | 3.3 | 24 | 7.4 |
| 15 | 3.5 | 24 | 10.6 |
| 16 | 3.5 | 24 | 10.9 |
| 17 | 3.7 | 24 | 17.2 |
| 18 | 3.7 | 24 | 18.5 |
| 19 | 3.3 | 72 | 5.1 |
| 20 | 3.3 | 72 | 5.3 |
| 21 | 3.5 | 72 | 7.2 |
| 22 | 3.5 | 72 | 7.1 |
| 23 | 3.7 | 72 | 13.3 |
| 24 | 3.7 | 72 | 16.6 |

The results show that for the blood volume of 2.5 ml mixed with 7.5 ml of stabilization buffer containing 3% (w/v) tetradecyltrimethylammonium oxalate and 125 mM or 200 mM tartaric acid, respectively, the pH of 3.7 is optimal for the yield and integrity of the total RNA. With all pH values, the stabilization of the RNA, judged by the integrity of the ribosomal RNA, was very good, but the yield of the isolated RNA was lower with the buffers adjusted to pH 3.3 and 3.5, respectively, than with the buffer adjusted to pH 3.7. However, even the lower yields achieved with the stabilization buffer adjusted to pH 3.3 were comparable or slightly better than the yields achieved with a control method, the RNA isolation with the QIAamp® RNA Blood Mini Kit (QIAGEN Cat. No. 52303), which showed an average yield of 6.8 µg RNA per 2.5 ml of blood.

EXAMPLE 2

Northern-Blot Analysis

This example shows the results of a Northern-Blot analysis performed with blood samples from three different donors stored at room temperature for 1 hour, 24 hours, 48 hours and 72 hours.

2.5 ml blood samples, drawn with a sodium citrate containing blood collection device, were mixed with 6.9 ml of stabilization buffer containing 4% (w/v) tetradecyltrimethylammonium oxalate and 200 mM tartaric acid in a 16×100 mm polyethylene tube. Samples were stored at room temperature for 1 hour, 24 hours, 48 hours, and 72 hours, respectively. In order to isolate the cellular RNA, the tubes were centrifuged at 5000×g for 10 minutes. The supernatant was discarded and the pellet was washed once with water. After additional centrifugation at 5000×g for 10 minutes, the pellet was dissolved in 300 µl of a lysis buffer, i.e., buffer RLT (QIAGEN GmbH), diluted with 360 µl water and 40 µl proteinase K were added. After a proteinase digestion for 10 minutes at 55° C. the sample was centrifuged at 20,000×g for 3 minutes, the supernatant was transferred into a new tube and 350 µl of 98% ethanol were added.

The sample was then applied to a silica membrane containing spin column by centrifugation at 8000×g for 1 minute. The spin column was washed once with a GITC containing washing buffer-like buffer RW1 (QIAGEN GmbH) and two times with an ethanol wash containing buffer-like buffer RPE (QIAGEN GmbH). The RNA was then eluted from the silica membrane with 2×40 µl of RNase free water. A single sample was prepared for each variable. 2.5 µg of the isolated RNA were loaded onto a denaturating agarose/formaldehyde gel, and after the electrophoresis the RNA was transferred onto a nylon membrane. The nylon membrane was hybridized subsequently with a radioactive labeled RNA probe, which contained the sequence of an IFN-gamma inducible gene (GeneBank Acc.No. L07633) overnight at 60° C., washed several times at 60° C. with washing buffers containing 2×SSC/0.1% SDS to 0.5×SSC/0.1% SDS. The nylon membrane was exposed subsequently to an X-ray film. As a control, RNA from the same donor was isolated using TRIzol™ LS reagent (Life Technologies) directly after the blood draw and analyzed as described above.

The results show that the transcript levels of the IFN-gamma inducible gene, which was used as a probe to hybridize the isolated RNA, was preserved over the entire time period with no visible change in the expression level. The transcript levels were equal to the TRIzol™ LS controls. These controls represent the in vivo conditions of the sample at the time point of the blood draw because the TRIzol reagent contains phenol combined with guanidine isothiocyanate and is considered as a reagent that destroys cells immediately, denatures proteins and therefore completely inhibits any biological activity. The comparison of the signal intensities from the stored samples with the TRIzol controls in the Northern-Blot analysis indicates that the transcript levels of the IFN-gamma inducible gene were "frozen" immediately after addition of the stabilization buffer to the blood sample and did not change any more during storage.

EXAMPLE 3

Comparison of Blood Collection Device with Conventional EDTA Tube

This example compares the stabilization of RNA with the collection device of the present invention and conventional EDTA containing tube.

2.5 ml blood, drawn from one donor with a blood collection device, containing 6.9 ml of stabilization buffer (4% (w/v) tetradecyltrimethylammonium oxalate, 200 mM tartaric acid, pH 3.7) in a 16×100 mm polyethylene tube closed with a HEMOGARD™ closure (Becton Dickinson and Company) and evacuated to a defined vacuum that draws 2.5 ml of blood when connected to the vein of the donor. Samples were stored at room temperature for 1 hour, 1 day, 3 days, 7 days and 10 days, respectively.

In order to isolate the cellular RNA, the tubes were centrifuged at 5000×g for 10 min. The supernatant was discarded and the pellet was washed once with water. After additional centrifugation at 5000×g for 10 min, the pellet was dissolved in 360 μl of a resuspension buffer containing ammonium acetate and then 300 μl of a lysis buffer, i.e., buffer RLT (QIAGEN GmbH), and 40 μl proteinase K were added. After a proteinase digestion for 10 minutes at 55° C., the sample was centrifuged at 20,000×g for 3 minutes, the supernatant was transferred into a new tube and 350 μl of 98% ethanol were added. The sample was then applied to a silica membrane containing spin column by centrifugation at 8000×g for 1 minute. The spin column was washed once with a GITC containing washing buffer-like buffer RW1 (QIAGEN GmbH) and two times with a ethanol containing buffer-like buffer RPE (QIAGEN GmbH).

A digestion of the residual genomic DNA which could be co-purified with the RNA in low amounts was performed on the silica membrane according to the instructions in the manual of the RNase-Free DNase Set (QIAGEN GmbH Cat. No. 79254). The RNA was eluted from the silica membrane with 2×40 μl of elution buffer. All samples were processed in duplicates. For the analysis, the eluates were diluted 1:125 fold and 1 μl of the diluted eluate was analyzed by real time TaqMan RT-PCR. The mRNA of the GAPDH-gene was amplified using an assay developed by Applied Biosystems (ABI). Each sample was analyzed in duplicate in the TaqMan RT-PCR amplification.

As a control, blood from the same donor was drawn with a Becton Dickinson Vacutainer EDTA tube and was stored in this tube for the same time period as described above. The RNA from 1 ml of the stored blood sample was isolated at each time point using TRIzol™ LS reagent (Life Technologies). The isolated RNA was subsequently cleaned up according to the RNeasy™ Mini protocol for the RNA clean up (QIAGEN Cat.No. 74103). The RNA was eluted with 2×40 μl of RNase-free water. The eluate was diluted 1:50 fold in order to compensate for the lower sample volume processed with the TRIzol method, compared, to the 2,5 ml of blood in the sample tubes. The samples were analyzed using also the GAPDH TaqMan RT-PCR system from Applied Biosystems (ABI).

Table 3 shows the results for the stabilization of cellular RNA in human blood. The real time RT-PCR results show that in the unpreserved EDTA blood, the transcript level decreases over time (indicated by the increasing ct value in the TaqMan analysis) up to a degree of degradation after 7 to 10 days at which point the mRNA is no longer detectable. On the other hand, the GAPDH mRNA in the preserved samples does not show any decrease in copy number, taking into consideration that the error range of the TaqMan assay is ±1 ct value. Within this error range, all changes in the ct value have to be considered as normal fluctuations of the amplification system and no degradation is visible. This result clearly indicates the advantage of the new developed blood collection device over the EDTA blood collection tube and also makes clear that the stabilization of the RNA is a prerequisite for the molecular analysis of the sample material.

TABLE 3

| storage at room temp. | NA stabilization device/ct value | mean value/ct | EDTA tube/ct value | mean value/ct |
|---|---|---|---|---|
| 1 h | 33.38 | 31.48 | 30.17 | 30.58 |
|  | 31.42 |  | 29.63 |  |
|  | 31.06 |  | 32.29 |  |
|  | 30.06 |  | 30.24. |  |
| 1 day | 31.28 | 30.11 | 30.18 | 31.26 |
|  | 28.62 |  | 29.35 |  |
|  | 30.34 |  | 33.2 |  |
|  | 30.19 |  | 32.32 |  |
| 3 days | 31.27 | 30.91 | 33.33 | 36.32 |
|  | 31.92 |  | 32.37 |  |
|  | 30.15 |  | 40 |  |
|  | 30.3 |  | 39.58 |  |
| 7 days | 33.03 | 32.58 | 40 | 38.4 |
|  | 31.16 |  | 39.01 |  |
|  | 34.21 |  | 37.67 |  |
|  | 31.9 |  | 36.12 |  |
| 10 days | 34.2 | 32.58 | 40 | 38.97 |
|  | 32.47 |  | 40 |  |
|  | 32.36 |  | 38.38 |  |
|  | 31.29 |  | 37.48 |  |

EXAMPLE 4

Stabilization of Genomic DNA in Whole Blood

It was also possible to isolate the genomic DNA from the stabilized blood sample. 2.5 ml blood, drawn with a sodium citrate containing blood collection device, were mixed with 6.9 ml of stabilization buffer containing 4% (w/v) tetradecyltrimethylammonium oxalate and 200 mM tartaric acid in a 16×100 mm polyethylene tube. Samples were stored at room temperature for 24 hours and 72 hours, respectively. In order to isolate the genomic DNA, the tubes were centrifuged at 5000×g for 10 min. The supernatant was discarded and the pellet was washed once with water. After additional centrifugation at 5000×g for 10 minutes, the pellet was dissolved in 300 μl of a EDTA and sodium chloride containing buffer and 400 μl of a lysis buffer, i.e., buffer AL (QIAGEN GmbH), and 20 μl proteinase K were added. After a proteinase digestion for 10 minutes at 65° C., 420 μl of 98% ethanol were added. The sample was then applied to a silica membrane containing spin column by centrifugation at 8000×g for 1 minute. The spin column was washed once with a guanidine hydrochloride containing washing buffer-like buffer AW1 (QIAGEN GmbH) and once with an ethanol containing buffer-like buffer AW2 (QIAGEN GmbH). The DNA was then eluted from the silica membrane with 300 μl of a tris-buffer.

5 μl of the eluate was analyzed on a 0.8% agarose/TBE gel stained with ethidium bromide. The yield of the isolated DNA was determined by measuring the optical density at 260 nm wavelength in a spectrophotometer and calculating that 1 OD260 corresponds to a concentration of 50 μg DNA/ml. After 24 hours and 72 hours of storage at room temperature, isolated genomic DNA was of high molecular weight. The main band migrated at a length greater than 20 kb. The yield was in the range of between 47 to 80 μg per 2.5 ml of blood, which is within the expected yield range for this amount of blood. The DNA was also applicable to enzymatic reactions like restriction endonuclease digestion and PCR amplification.

The genomic DNA was also applied to enzymatic reactions like restriction enzyme digestion or PCR amplification. For the restriction endonuclease digestion, 2 μg of the DNA was digested with 6 U EcoRI (E) and Hind III (H), respectively, for 3 hours at 37° C. and analyzed subsequently on a 0.8% agarose TBE gel. For the PCR amplification, 150 and 300 ng of the DNA were added to a 50 µl total volume PCR reaction mix and a 1.1 kb fragment of the human homologue of giant larvae-gene was amplified. The PCR products were analyzed on a 1.2-% agarose/TBE gel.

EXAMPLE 5

This example demonstrates the inherent instability and transcription of RNA in a biological sample when the sample is stored at room temperature in the absence of stabilizing agents. Whole blood samples were collected from four human donors identified as donors 1, 2, 3 and 4. For each donor, a first group of samples was drawn in a EDTA blood collection tube and stored at −70° C. A second group of samples was collected in an identical EDTA blood collection tube and stored at room temperature.

The second group of samples was stored under identical conditions at room temperature and analyzed at 1, 3, 5 and 7 days for total interferon-gamma mRNA by quantitative TaqMan RT-PCR. The first group of samples was stored under identical conditions at −70° C. and analyzed for total interferon-gamma mRNA by quantitative TaqMan RT-PCR. The measured mRNA content of each sample is shown in the graphs of FIGS. 2–5 for donors 1–4, respectively. As shown in the graphs, the blood samples stored at −70° C. exhibit a small decrease in the total amount of interferon-gamma mRNA after day 1. Three of the samples at −70° C. showed a slight increase in mRNA between day 1 and day 5 which can be interpreted as variation in the error range of the technology.

The blood samples stored with EDTA at room temperature exhibited a significant increase in total interferon-gamma mRNA after three days indicating a high rate of gene induction. After day 3, the samples exhibited a decrease in the total interferon-gamma mRNA indicating significant decomposition. The data of this example demonstrate that whole blood treated with EDTA at room temperature is not stable and that the total mRNA in the sample continuously changes as a result of gene induction and decomposition. The constant changes of the total mRNA in the sample prevents an accurate determination and analysis of mRNA originally in the blood sample.

EXAMPLE 6

This example compares the changes over time of certain interleukin mRNA species and other mRNA species in a whole blood control sample combined with EDTA and stored at room temperature, and whole blood test sample stabilized with a composition of tetradecyltrimethylammonium oxalate and tartaric acid and stored at room temperature. The blood samples were obtained directly from the same subjects and combined immediately with the respective stabilizing agent. The resulting samples were stored under identical conditions at room temperature.

The collection device was a 16×100 mm polyethylene tube containing 6.9 ml of stabilization buffer containing 4% (w/v) tetradecyltrimethylammonium oxalate and 200 mM tartaric acid. The blood samples were drawn directly from the donor into the collection device where they were mixed immediately with the tetradecyltrimethylammonium oxalate and the tartaric acid. The control sample was prepared with 2.5 ml of fresh drawn blood in a Becton Dickinson Vacutainer EDTA tube. At selected time intervals, the control sample and the test sample were analyzed by quantitative TaqMan RT-PCR as in the previous examples.

FIGS. 6–9 are graphs showing the changes over time in the amount of specified interleukin mRNA species and other mRNA species in the blood samples. The samples were analyzed by standard procedures for measuring the amount of the mRNA species immediately after collection of the blood samples to establish a base line.

Figure 6:
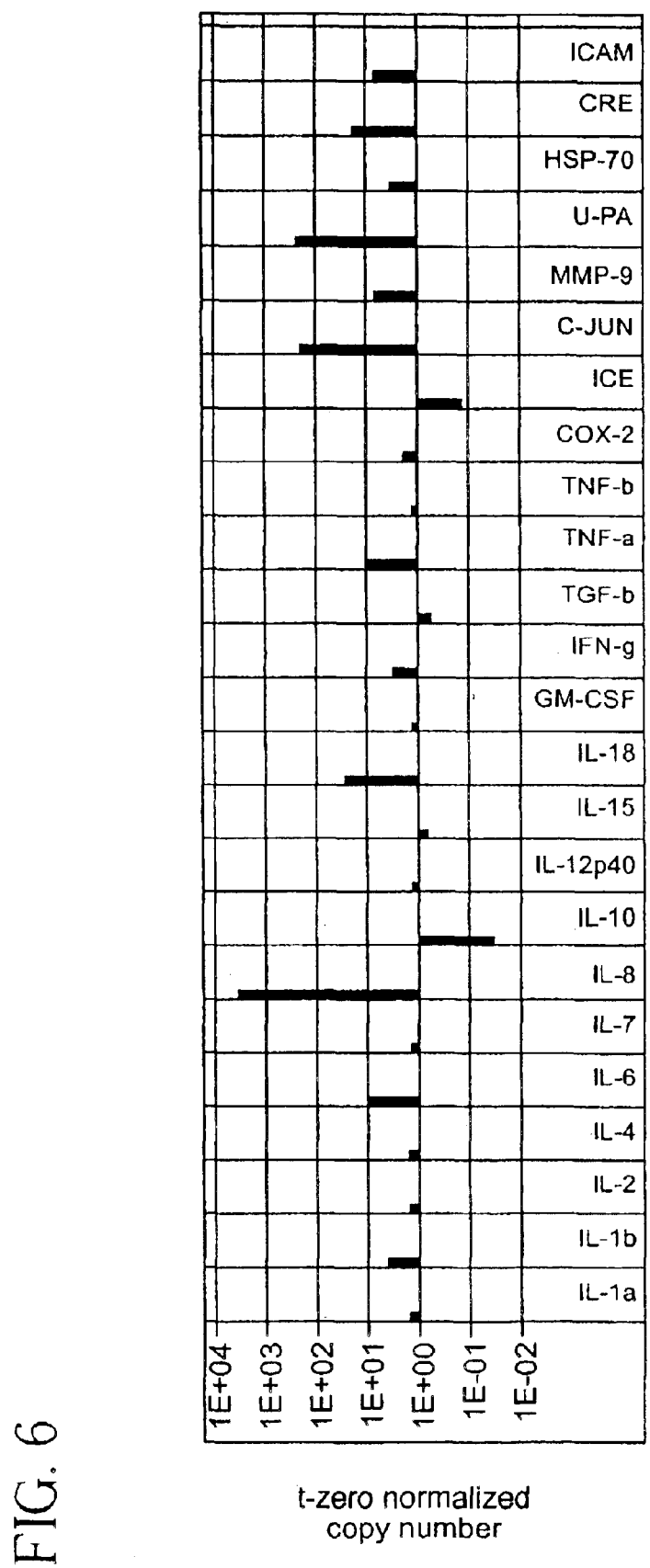
FIG. 6 is a graph of the amounts of certain interleukin and other mRNA species in whole blood over a five day period of a blood sample without a stabilizing reagent.

The samples were stored at room temperature and analyzed at 4 hours, 8 hours, 24 hours, 3 days and 5 days. FIG. 6 shows the amount of the mRNA species in the blood sample mixed with EDTA, after storage for 5 days as measured by the change from the base line. The specific mRNA species measured are identified in the bottom portion of the graph along the horizontal axis. The vertical axis indicates the change in the amount of the mRNA species and measured in changes by orders of magnitude. As shown in FIG. 6, several mRNA species exhibited little or no change after 5 days, while certain other mRNA species exhibited significant increases or decreases. The increases are understood to be the result of gene induction while the decreases are the result of degradation.

Figure 7:
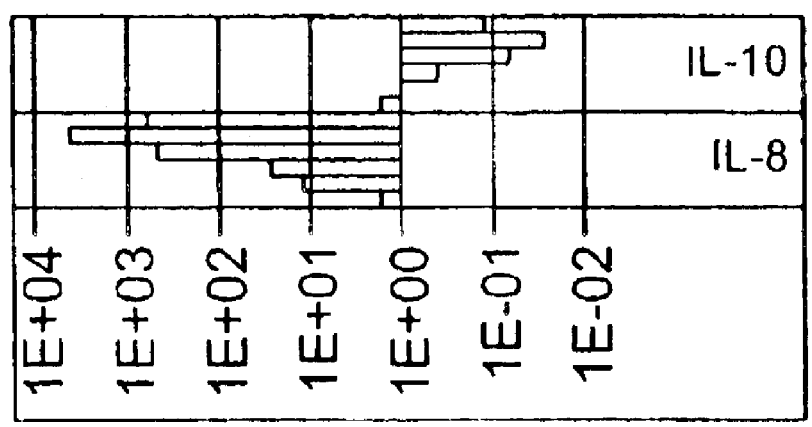
FIG. 7 is a graph showing the changes in the amount of IL-8 and IL-10 mRNA over a five day period of a blood sample without a stabilizing agent.

The graph of FIG. 7 shows the changes in the amount of IL-8 and IL-10 transcripts for the blood sample stabilized with EDTA. The amount of the transcripts were measured at 4 hours, 8 hours, 24 hours, 3 days and 5 days as shown by each bar of the graph. As shown, the amount of IL-8 mRNA present in the sample increases at a steady rate during the first three days as a result of gene induction and then starts to decrease as a result of decomposition. In contrast, the IL-10 mRNA level shows a decrease during the first three days followed by a small increase at day 5 compared to day 3. The data presented in FIG. 7 demonstrate instability of a blood sample stored at room temperature with EDTA.

Figure 8:
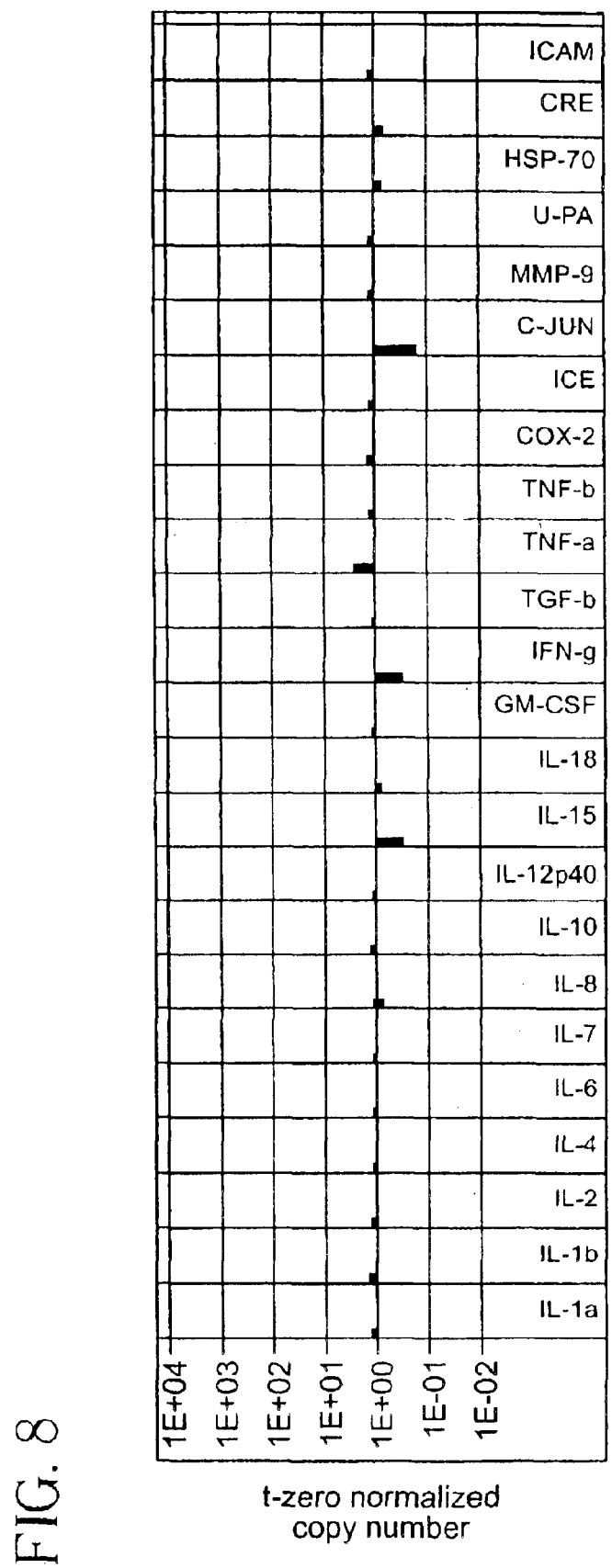
FIG. 8 is a graph showing the amounts of certain mRNA species in whole blood over a five day period stored at room temperature with tetradecyltrimethyl-ammonium oxalate and tartaric acid.

The blood test sample stabilized with a composition of tetradecyltrimethyl-ammonium oxalate and tartaric acid was analyzed immediately after collection to measure the quantity of the mRNA species and establish a base line. The samples were analyzed again after three days where the samples were stored at room temperature (about 18–22° C.). The results are presented in the graph of FIG. 8 showing the changes in the mRNA species. As demonstrated by these data, the mRNA species in the blood sample exhibited significantly smaller changes compared to the blood sample stabilized with EDTA.

Figure 9:
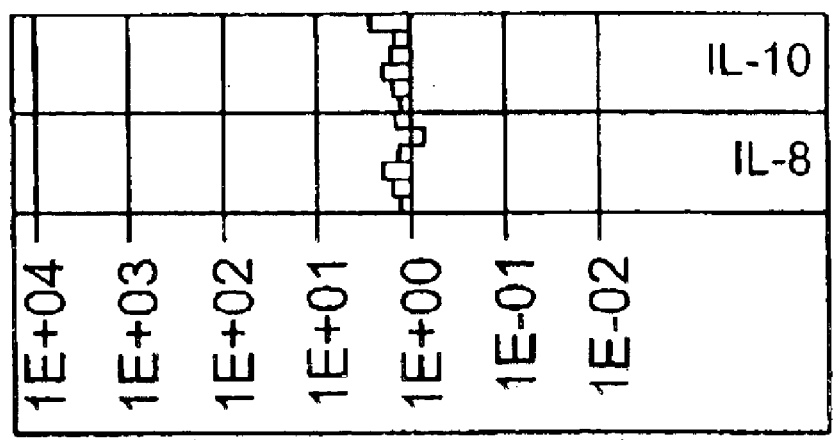
FIG. 9 is a graph showing the changes in the amount of IL-8 and IL-10 in theسa sample of FIG. 8 over a five day period.

FIG. 9 is a graph showing the changes in the amount of IL-8 mRNA and IL-10 mRNA over five days when measured at 4 hours, 8 hours, 24 hours, 3 days and 5 days. The data demonstrate only very small changes in the IL-8 mRNA level compared to the very significant changes in the EDTA whole blood samples described in FIG. 7. The amount of IL-10 mRNA is shown to exhibit a gradual increase after five days, whereas very significant changes had been determined in the EDTA whole blood samples (FIG. 7).

While various embodiments have been chosen to demonstrate the invention, it will be understood by those skilled in the art that various modifications and additions can be made without departing from the scope of the invention as defined in the appended claims.

What is claimed is:

1. An apparatus for collecting and stabilizing a biological sample containing nucleic acids, said apparatus comprising:
   a container defining an internal chamber dimensioned for receiving said biological sample, said container having an open end and a closure closing said open end, and
   a gene induction blocking agent and a proton donor contained within said container in an amount effective to block ex vivo gene induction in said biological sample and to stabilize said biological sample against enzymatic degradation of nucleic acids, where said gene induction blocking agent is a cationic compound or a detergent.

2. The apparatus of claim 1, wherein said gene induction blocking agent and said proton donor are in an aqueous medium having a pH of about pH 2 to about pH 12.

3. The apparatus of claim 2, wherein said aqueous medium has a pH of about pH 2 to about pH 10.

4. The apparatus of claim 2, wherein said aqueous medium has a pH of about pH 3 to about pH 8.

5. The apparatus of claim 1, wherein said gene induction blocking agent is a solid compound in said container.

6. The apparatus of claim 1, wherein said gene induction blocking agent comprises a stabilizing agent having the formula $$YR_1R_2R_3R_4\ X$$

wherein Y is nitrogen or phosphorous;

$R_1$, $R_2$, $R_3$, and $R_4$ are independently selected from the group consisting of branched alkyl, non-branched alkyl, $C_6$–$C_{20}$ aryl, and $C_6$–$C_{26}$ aralkyl; and X is an anion.

7. The apparatus of claim 6, wherein said branched alkyl is a $C_3$–$C_{20}$ alkyl and said non-branched alkyl is a $C_1$–$C_{20}$ alkyl.

8. The apparatus of claims 6, wherein X is an anion selected from the group consisting of phosphate, sulfate, formate, acetate, propionate, oxalate, malonate, succinate, citrate, bromide and chloride.

9. The apparatus of claim 6, wherein Y is nitrogen and said stabilizing agent is a quaternary amine.

10. The apparatus of claim 6, wherein said $R_1$ is an alkyl having 12, 14, or 16 carbon atoms and $R_2$, $R_3$, and $R_4$ are methyl.

11. The apparatus of claim 1, wherein said container has an internal pressure less than atmospheric pressure, for drawing a predetermined volume of said biological sample into said container.

12. The apparatus of claim 1, wherein said gene induction blocking agent is included in an amount to lyse cells in said biological sample.

13. The apparatus of claim 1, wherein said gene induction blocking agent lyses reticulocytes, bacteria, red blood cells, and white blood cells.

14. The apparatus of claim 1, wherein said detergent is selected from the group consisting of sodium dodecylsulfate and polyoxyethylene sorbitan monolaurate.

15. The apparatus of claim 1, wherein said proton donor is selected from the group consisting of carboxylic acids and mineral acids.

16. The apparatus of claim 15, wherein said proton donor is selected from the group consisting of alkenyl carboxylic acids, aliphatic monocarboxylic acids, aliphatic dicarboxylic acids, and aliphatic tricarboxylic acids.

17. The apparatus of claim 1, wherein said proton donor is selected from the group consisting of alkenyl carboxylic acids, $C_1$–$C_6$ aliphatic monocarboxylic acids, aliphatic $C_2$–$C_6$ dicarboxylic acids, tricarboxylic acids, hydroxy-monocarboxylic acids, hydroxy-dicarboxylic acids, hydroxy-tricarboxylic acids, aliphatic keto-monocarboxylic acids, aliphatic keto-dicarboxylic acids, amino acids, and mixtures thereof.

* * * * *